United States Patent [19]

Wolfgram

[11] 4,023,931
[45] May 17, 1977

[54] MEANS AND METHOD FOR MEASURING LEVELS OF IONIC CONTAMINATION

[75] Inventor: Edgar W. Wolfgram, Glen Ellyn, Ill.

[73] Assignee: Kenco Alloy & Chemical Co. Inc., Addison, Ill.

[22] Filed: Feb. 17, 1976

[21] Appl. No.: 658,182

[52] U.S. Cl. .......................... 23/230 R; 23/253 R; 324/71 R
[51] Int. Cl.² ...................................... G01N 27/06
[58] Field of Search ........... 23/230 R, 253; 324/62, 324/71 R; 204/1 T

[56] References Cited

UNITED STATES PATENTS

| 3,366,554 | 1/1968 | Lindblad | 23/230 R |
| 3,459,505 | 8/1969 | Tweed | 23/230 R |
| 3,490,873 | 1/1970 | Corl | 23/230 R |

Primary Examiner—R.E. Serwin
Attorney, Agent, or Firm—Kinzer, Plyer, Dorn & McEachran

[57] ABSTRACT

A system and method for measuring ionic contamination of an electronic assembly includes the steps of providing a test solution of a known ionic content; placing an electronic assembly of known exposed area into a predetermined static volume of the test solution; thereafter measuring the ionic content of the test solution to provide a measurement of the ionic contamination of said assembly.

11 Claims, 1 Drawing Figure

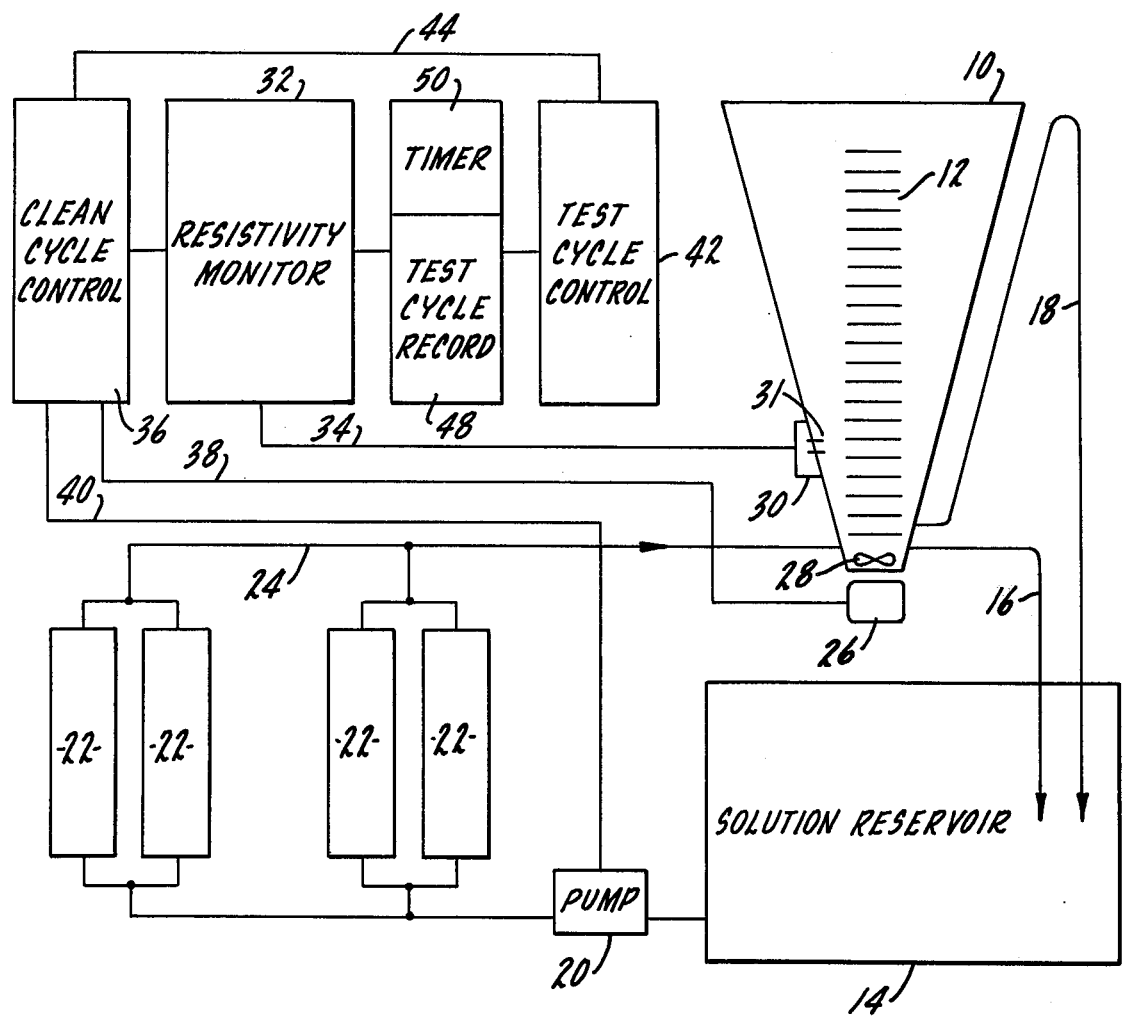

MEANS AND METHOD FOR MEASURING LEVELS OF IONIC CONTAMINATION

SUMMARY OF THE INVENTION

The present invention relates to a method and apparatus for measuring the ionic contamination of an electronic assembly, for example a printed circuit board.

A primary purpose of the invention is a system of the type described including the steps of first bringing a test solution to a predetermined level of ionic purity, and thereafter placing a printed circuit board of known area into a known volume of such solution to provide a measurement of the ionic contamination of the board.

Another purpose is a system of the type described in which the ion content of the solution is determined by measuring the resistivity of the solution between two predetermined spaced points.

Another purpose is a method of the type described including the step of agitating the fluid within the test cell so as to provide homogeneity.

Another purpose is a system of the type described which is used to determine the reliability of the normal cleaning processes of electronic assemblies, for example printed circuit boards.

Another purpose is a system of the type described which includes the preliminary step of bringing the test solution to a known ionic content and thereafter using a predetermined static volume of the solution to determine the ionic contamination of an assembly within the solution.

Other purposes will appear in the ensuing specification, drawing and claims.

BRIEF DESCRIPTION OF THE DRAWINGS

The invention is illustrated diagrammatically in the attached schematic diagram.

DESCRIPTION OF THE PREFERRED EMBODIMENT

A test cell or test tank is indicated generally at 10 and may have a tapered or wedge-shaped construction and volume graduations 12 along one side thereof. The shape of the tank is particularly desirable for the insertion of printed circuit boards or other electronic assemblies which are to be treated in the manner described. Tank 10 is connected to a solution reservoir 14 through a drain line 16 and a purge line 18. A pump 20 is connected between solution reservoir 14 and the parallel combination of four ion removal columns 22 which may be of the type manufactured by the Barnstead Division of Sybron Corp., Boston, Mass. Such ion removal columns are known as a "mixed bed" type in that the particles within the column will remove both positive and negative ions from the solution passing therethrough. The upper ends of columns 22 are connected through a line 24 to the bottom of tank 10 to complete the fluid circuit.

A motor 26 is positioned directly beneath the bottom of tank 10 and in direct alignment with an agitator 28 which may be in the form of a magnet positioned in the bottom of the tank. As the motor rotates the magnet will similarly rotate, thus providing an agitation for solution within test cell or tank 10.

An electronic sensor is indicated diagrammatically at 30 and may be of the type having a pair of spaced plates or probes 31 which are maintained a predetermined distance apart and which may have a voltage impressed across them. Such sensors are manufactured by Balsbaugh Laboratories, Hingham, Mass.

A resistivity monitor circuit is indicated diagrammatically at 32 and is connected by a line 34 to sensor 30. Thus, the resistivity monitor will provide a direct indication, in ohms, of the ionic content of the solution within tank 10. The resistivity monitor will measure the resistance between spaced elements 31 in sensor 30, with this resistance being directly determined by the ionic content of the solution within the tank. Clean cycle control circuit 36 is connected by a line 38 to motor 26 and by a line 40 to pump 20. A test cycle control circuit 42 is connected by line 44 to clean cycle control 36. A test cycle record circuit 48 and a timer 50 are each connected to the resistivity monitor 32 and the test cycle control 42. In like manner, the resistivity monitor 32 is connected to clean cycle control 36.

The method and system described herein is useful in determining the ionic contamination of electronic assemblies, for example printed circuit boards. Such boards are customarily cleaned after soldering operations, which cleaning operation is to remove as much as possible of the various contaminants which are caused by the soldering process. Such ionic contamination, both positive and negative ions, can cause subsequent corrosion if not removed from the printed circuit board.

The processes used by the manufacturers of printed circuit boards normally will provide substantially clean boards. The present invention is directed to a means for testing the reliability of such cleaning processes.

Basically the invention contemplates two distinct operating steps. In the first step the test solution is brought to a predetermined purity level. In the second step a predetermined static volume of the purified solution receives a printed circuit board of known exposed cross sectional area and the change in ion content of the solution is recorded giving a direct indication of the ionic contamination remaining on the printed circuit board after the normal cleaning process.

Looking particularly at the first step in the described method, solution from reservoir 14 will flow through ion removal columns 22 and through line 24 to the bottom of tank 10. The solution within the tank will gradually rise until it has reached the same level as the top of purge line 18. At this point the suction through the purge line will cause the tank to be emptied into solution reservoir 14. During the period that there is solution within tank 10, the resistivity of the solution will be measured by sensor 30 and resistivity monitor 32. Clean cycle control 36 will continue to cause pump 20 and agitation motor 26 to operate until the solution purity, as measured by the resistivity monitor, reaches a predetermined level. This level may be set in a conventional manner by switch controls on clean cycle control 36. Once the desired purity level is reached, the pump will stop and the solution will no longer be circulated in the manner described.

Test cycle control 42 is now activated which, through clean cycle control 36, will cause pump 20 to place a predetermined volume of test solution within tank 10. The volume placed within tank 10 is determined by the exposed cross sectional area of the printed circuit board or boards which are to be tested. Graduations 12 can be scaled to read directly in board area or they may be scaled in volume. In any event, pump 20 will place a predetermined volume of fluid within tank 10 as the pump is controlled by test cycle control 42 and clean cycle control 36. Once the desired volume of fluid has been placed within the tank, the pump is stopped. The printed circuit boards or other electronic assemblies are immersed in the tank and resistivity monitor 32 through sensor 30 will give a direct indication of the change in resistivity of the fluid which is directly caused by the ionic contamination of the immersed boards. Timer 50 and test cycle record 48 may be utilized to record the change in resistivity and to control the time in which the change in resistivity is measured. After the predetermined test interval and the recording of the change in resistivity of the solution within tank 10, the printed circuit boards may be removed. The change in solution purity is a direct indication of the ionic contamination of the board after it has passed through the conventional cleaning process and thus provides a direct indication of the reliability and efficiency of such cleaning processes. Tank 10 may now be drained through drain line 16 directing the solution back to reservoir 14.

The test solution may vary widely. A basic solution of a 50—50 mixture of reagent grade isopropyl alcohol and de-ionized water has been found to be satisfactory.

Ion removal columns 22 may all be connected in parallel as shown or there may be suitable valve means for directing solution through one pair of columns or through the other, thus providing for easy replacement of a column once it is spent.

Whereas the preferred form of the invention has been shown and described herein, it should be realized that there may be many modifications, substitutions and alterations thereto.

The embodiments of the invention in which an exclusive property or privilege is claimed are defined as follows:

1. A method for measuring the ionic contamination of an electronic assembly including the steps of providing a test solution of a known ionic content, placing an electronic assembly of known exposed area into a predetermined static volume of the test solution, thereafter measuring the ionic content of the test solution to provide a measurement of the ionic contamination of said assembly.

2. The method of claim 1 further characterized in that the step of providing a test solution of a known ionic content includes the subsidiary step of cycling the test solution through an ion removal system while continuously monitoring the ionic content of the solution.

3. The method of claim 1 further characterized in that said test solution is passed successively through a reservoir, an ion removal system and a test cell in bringing the test solution to a known ionic content.

4. The method of claim 1 further characterized by and including the step of timing the period in which the electronic assembly remains in the known volume of test solution.

5. The method of claim 1 further characterized by and including the step of agitating the test solution during the step of providing such a solution of a known ionic content and during the period that the electronic assembly is within the test solution.

6. The method of claim 1 further characterized in that the ionic content of the solution is determined by measuring the resistivity of the solution between electronic sensors positioned a predetermined distance apart.

7. A system for measuring the ionic contamination of an electronic assembly including a test cell formed and adapted to contain an electronic assembly, a solution reservoir and ion removal means in fluid circuit with said test cell, a pump for circulating fluid through said circuit and test cell, means for measuring the ionic contamination of solution within said cell, and control means for causing said pump to cycle fluid through said test cell, ion removal means and reservoir, said control means further including means for causing said pump to place a predetermined static volume of fluid within said test cell.

8. The system of claim 7 further characterized in that said measuring means includes an electronic sensor for measuring the resistivity of said solution between a pair of spaced electrodes.

9. The system of claim 7 further characterized by and including means for agitating solution within said test cell to provide a homogeneous fluid.

10. The structure of claim 9 further characterized in that said agitating means includes a magnet positioned within the test cell and a motor positioned outside of the test cell and directly adjacent the magnet.

11. The system of claim 7 further characterized in that said ion removal means includes a plurality of ion columns connected in parallel between said reservoir and test cell.

* * * * *